(12) United States Patent
Naidu et al.

(10) Patent No.: US 7,224,763 B2
(45) Date of Patent: May 29, 2007

(54) METHOD OF AND SYSTEM FOR X-RAY SPECTRAL CORRECTION IN MULTI-ENERGY COMPUTED TOMOGRAPHY

(75) Inventors: Ram Naidu, Waban, MA (US); Zhengrong Ying, Wakefield, MA (US); Chitra Subramanian, Salem, MA (US); Sergey Simanovsky, Brookline, MA (US); Carl R. Crawford, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 205 days.

(21) Appl. No.: 10/899,775

(22) Filed: Jul. 27, 2004

(65) Prior Publication Data

US 2006/0023844 A1 Feb. 2, 2006

(51) Int. Cl.
*G01N 23/00* (2006.01)
(52) U.S. Cl. .......................................... 378/5; 378/210
(58) Field of Classification Search ................ 378/210, 378/156–159, 207, 901, 5, 57
See application file for complete search history.

(56) References Cited

U.S. PATENT DOCUMENTS

| | | | |
|---|---|---|---|
| 3,562,525 A * | 2/1971 | Constantine et al. | ......... 378/48 |
| 4,029,963 A | 6/1977 | Alvarez et al. | |
| 4,361,900 A * | 11/1982 | Siedband | ..................... 378/98 |
| 4,759,047 A | 7/1988 | Donges et al. | |
| 4,884,289 A | 11/1989 | Glockmann et al. | |
| 4,933,960 A * | 6/1990 | Fujisaki | ..................... 378/53 |
| 5,132,998 A | 7/1992 | Tsutsui et al. | |
| 5,182,764 A | 1/1993 | Peschmann et al. | |
| 5,247,561 A | 9/1993 | Kotowski | |
| 5,319,547 A | 6/1994 | Krug et al. | |
| 5,367,552 A | 11/1994 | Peschmann et al. | |
| 5,473,657 A | 12/1995 | McKenna | |
| 5,490,218 A | 2/1996 | Krug et al. | |
| 5,661,774 A | 8/1997 | Gordon et al. | |
| 5,802,134 A | 9/1998 | Larson et al. | |
| 5,878,111 A * | 3/1999 | Schulz | ..................... 378/158 |
| 5,881,122 A | 3/1999 | Ruth et al. | |
| 5,887,047 A | 3/1999 | Ruth et al. | |
| 5,901,198 A | 5/1999 | Ruth et al. | |
| 5,909,477 A | 6/1999 | Ruth et al. | |
| 5,932,874 A | 8/1999 | Legg et al. | |
| 5,937,028 A | 8/1999 | Tybinkowski et al. | |

(Continued)

FOREIGN PATENT DOCUMENTS

DE 3150306 12/1981

*Primary Examiner*—Courtney Thomas
*Assistant Examiner*—Alexander Taningco
(74) *Attorney, Agent, or Firm*—McDermott Will & Emery LLP

(57) ABSTRACT

A method of and a system for spectral correction in multi-energy computed tomography are provided to correct reconstructed images, including high-energy CT images and Z (effective atomic number) images, for spectral variations, which include time variations on a scanner due to HVPS drift and scanner to scanner variations due to the beamline component differences. The method uses a copper filter mounted on the detector array for tracking the spectral changes. The method comprises: generating copper ratios; computing working air tables; calculating scales and offsets; and correcting high-energy CT images and Z images using calculated scales and offsets. The method further includes an off-line calibration procedure to generate necessary parameters for the online correction.

11 Claims, 10 Drawing Sheets

U.S. PATENT DOCUMENTS

| | | |
|---|---|---|
| 5,949,842 A | 9/1999 | Schafer et al. |
| 5,970,113 A | 10/1999 | Ruth et al. |
| 5,982,843 A | 11/1999 | Bailey et al. |
| 5,982,844 A | 11/1999 | Tybinkowski et al. |
| 6,026,143 A | 2/2000 | Simanovsky et al. |
| 6,026,171 A | 2/2000 | Hiraoglu et al. |
| 6,035,014 A | 3/2000 | Hiraoglu et al. |
| 6,067,366 A | 5/2000 | Simanovsky et al. |
| 6,075,871 A | 6/2000 | Simanovsky et al. |
| 6,076,400 A | 6/2000 | Bechwati et al. |
| 6,078,642 A | 6/2000 | Simanovsky et al. |
| 6,091,795 A | 7/2000 | Schafer et al. |
| 6,108,396 A | 8/2000 | Bechwati et al. |
| 6,111,974 A | 8/2000 | Hiraoglu et al. |
| 6,128,365 A | 10/2000 | Bechwati et al. |
| 6,195,444 B1 | 2/2001 | Simanovsky et al. |
| 6,256,404 B1 | 7/2001 | Gordon et al. |
| 6,272,230 B1 | 8/2001 | Hiraoglu et al. |
| 6,345,113 B1 | 2/2002 | Crawford et al. |
| 6,687,326 B1 | 2/2004 | Bechwati et al. |
| 6,721,387 B1 | 4/2004 | Naidu et al. |
| 2004/0264628 A1* | 12/2004 | Besson ............ 378/5 |

* cited by examiner

METHOD OF AND SYSTEM FOR X-RAY SPECTRAL CORRECTION IN MULTI-ENERGY COMPUTED TOMOGRAPHY

RELATED APPLICATIONS

This patent application and/or patents are related to the following co-pending U.S. applications and/or issued U.S. patents, of the assignee as the present application, the contents of which are incorporated herein in their entirety by reference:

"Nutating Slice CT Image Reconstruction Apparatus and Method," invented by Gregory L. Larson, et al., U.S. application Ser. No. 08/831,558, filed on Apr. 9, 1997, now U.S. Pat. No. 5,802,134, issued on Sep. 1, 1998;

"Computed Tomography Scanner Drive System and Bearing," invented by Andrew P. Tybinkowski, et al., U.S. application Ser. No. 08/948,930, filed on Oct. 10, 1997, now U.S. Pat. No. 5,982,844, issued on Nov. 9, 1999;

"Air Calibration Scan for Computed Tomography Scanner with Obstructing Objects," invented by David A. Schafer, et al., U.S. application Ser. No. 08/948,937, filed on Oct. 10, 1997, now U.S. Pat. No. 5,949,842, issued on Sep. 7, 1999;

"Computed Tomography Scanning Apparatus and Method With Temperature Compensation for Dark Current Offsets," invented by Christopher C. Ruth, et al., U.S. application Ser. No. 08/948,928, filed on Oct. 10, 1997, now U.S. Pat. No. 5,970,113, issued on Oct. 19, 1999;

"Computed Tomography Scanning Target Detection Using Non-Parallel Slices," invented by Christopher C. Ruth, et al., U.S. application Ser. No. 08/948,491, filed on Oct. 10, 1997, now U.S. Pat. No. 5,909,477, issued on Jun. 1, 1999;

"Computed Tomography Scanning Target Detection Using Target Surface Normals," invented by Christopher C. Ruth, et al., U.S. application Ser. No. 08/948,929, filed on Oct. 10, 1997, now U.S. Pat. No. 5,901,198, issued on May 4, 1999;

"Parallel Processing Architecture for Computed Tomography Scanning System Using Non-Parallel Slices," invented by Christopher C. Ruth, et al., U.S. application Ser. No. 08/948,697, filed on Oct. 10, 1997, U.S. Pat. No. 5,887,047, issued on Mar. 23, 1999;

"Computed Tomography Scanning Apparatus and Method For Generating Parallel Projections Using Non-Parallel Slice Data," invented by Christopher C. Ruth, et al., U.S. application Ser. No. 08/948,492, filed on Oct. 10, 1997, now U.S. Pat. No. 5,881,122, issued on Mar. 9, 1999;

"Computed Tomography Scanning Apparatus and Method Using Adaptive Reconstruction Window," invented by Bernard M. Gordon, et al., U.S. application Ser. No. 08/949,127, filed on Oct. 10, 1997, now U.S. Pat. No. 6,256,404, issued on Jul. 3, 2001;

"Area Detector Array for Computed Tomography Scanning System," invented by David A Schafer, et al., U.S. application Ser. No. 08/948,450, filed on Oct. 10, 1997, now U.S. Pat. No. 6,091,795, issued on Jul. 18, 2000;

"Closed Loop Air Conditioning System for a Computed Tomography Scanner," invented by Eric Bailey, et al., U.S. application Ser. No. 08/948,692, filed on Oct. 10, 1997, now U.S. Pat. No. 5,982,843, issued on Nov. 9, 1999;

"Measurement and Control System for Controlling System Functions as a Function of Rotational Parameters of a Rotating Device," invented by Geoffrey A. Legg, et al., U.S. application Ser. No. 08/948,493, filed on Oct. 10, 1997, now U.S. Pat. No. 5,932,874, issued on Aug. 3, 1999;

"Rotary Energy Shield for Computed Tomography Scanner," invented by Andrew P. Tybinkowski, et al., U.S. application Ser. No. 08/948,698, filed on Oct. 10, 1997, now U.S. Pat. No. 5,937,028, issued on Aug. 10, 1999;

"Apparatus and Method for Detecting Sheet Objects in Computed Tomography Data," invented by Muzaffer Hiraoglu, et al., U.S. application Ser. No. 09/022,189, filed on Feb. 11, 1998, now U.S. Pat. No. 6,111,974, issued on Aug. 29, 2000;

"Apparatus and Method for Eroding Objects in Computed Tomography Data," invented by Sergey Simanovsky, et al., U.S. application Ser. No. 09/021,781, filed on Feb. 11, 1998, now U.S. Pat. No. 6,075,871, issued on Jun. 13, 2000;

"Apparatus and Method for Combining Related Objects in Computed Tomography Data," invented by Ibrahim M. Bechwati, et al., U.S. application Ser. No. 09/022,060, filed on Feb. 11, 1998, now U.S. Pat. No. 6,128,365, issued on Oct. 3, 2000;

"Apparatus and Method for Detecting Sheet Objects in Computed Tomography Data," invented by Sergey Simanovsky, et al., U.S. application Ser. No. 09/022,165, filed on Feb. 11, 1998, now U.S. Pat. No. 6,025,143, issued on Feb. 15, 2000;

"Apparatus and Method for Classifying Objects in Computed Tomography Data Using Density Dependent Mass Thresholds," invented by Ibrahim M. Bechwati, et al., U.S. application Ser. No. 09/021,782, filed on Feb. 11, 1998, now U.S. Pat. No. 6,076,400, issued on Jun. 20, 2000;

"Apparatus and Method for Correcting Object Density in Computed Tomography Data," invented by Ibrahim M. Bechwati, et al., U.S. application Ser. No. 09/022,354, filed on Feb. 11, 1998, now U.S. Pat. No. 6,108,396, issued on Aug. 22, 2000;

"Apparatus and Method for Density Discrimination of Objects in Computed Tomography Data Using Multiple Density Ranges," invented by Sergey Simanovsky, et al., U.S. application Ser. No. 09/021,889, filed on Feb. 11, 1998, now U.S. Pat. No. 6,078,642, issued on Jun. 20, 2000;

"Apparatus and Method for Detection of Liquids in Computed Tomography Data," invented by Muzaffer Hiraoglu, et al., U.S. application Ser. No. 09/022,064, filed on Feb. 11, 1998, now U.S. Pat. No. 6,026,171, issued on Feb. 15, 2000;

"Apparatus and Method for Optimizing Detection of Objects in Computed Tomography Data," invented by Muzaffer Hiraoglu, et al., U.S. application Ser. No. 09/022,062, filed on Feb. 11, 1998, now U.S. Pat. No. 6,272,230, issued on Aug. 7, 2001;

"Multiple-Stage Apparatus and Method for Detecting Objects in Computed Tomography Data," invented by Muzaffer Hiraoglu, et al., U.S. application Ser. No. 09/022,164, filed on Feb. 11, 1998, now U.S. Pat. No. 6,035,014, issued on Mar. 7, 2000;

"Apparatus and Method for Detecting Objects in Computed Tomography Data Using Erosion and Dilation of Objects," invented by Sergey Simanovsky, et al., U.S. application Ser. No. 09/022,204, filed on Feb. 11, 1998, now U.S. Pat. No. 6,067,366, issued on May 23, 2000;

"Apparatus and method for processing object data in computed tomography data using object projections," invented by Carl R. Crawford, et al, U.S. application Ser. No. 09/228,379, filed on Jan. 12, 1999, now U.S. Pat. No. 6,345,113, issued on Feb. 5, 2002;

"Apparatus and method for detecting concealed objects in computed tomography data," invented by Sergey Simanovsky, et al., U.S. application Ser. No. 09/228,380, filed on Jan. 12, 1999, now U.S. Pat. No. 6,195,444, issued on Feb. 27, 2001;

"Method of and system for correcting scatter in a computed tomography scanner," invented by Ibrahim M. Bechwati, et al, U.S. application Ser. No. 10/121,466, filed on Apr. 11, 2002, now U.S. Pat. No. 6,687,326, issued on Feb. 3, 2004;

"Method of and system for reducing metal artifacts in images generated by x-ray scanning devices," invented by Ram Naidu, et al, U.S. application Ser. No. 10/171,116, filed on Jun. 13, 2002, now U.S. Pat. No. 6,721,387, issued on Apr. 13, 2004;

"Method and apparatus for automatic image quality assessment," invented by Seemeen Karimi, et al, U.S. application Ser. No. 09/842,075, filed on Apr. 25, 2001.

"Decomposition of Multi-Energy Scan Projections using Multi-Step Fitting," invented by Ram Naidu, et al, U.S. application Ser. No. 10/611,572, filed on Jul. 1, 2003;

"Method of and system for detecting threat objects using computed tomography images," invented by Zhengrong Ying, et al, U.S. application Ser. No. 10/831,909, filed on Apr. 26, 2004.

"Method of and system for computing effective atomic number image in multi-energy computed tomography," invented by Zhengrong Ying, et al, U.S. application Ser. No. 10/850,910, filed on May 21, 2004;

"Method of and system for adaptive scatter correction in multi-energy computed tomography," invented by Zhengrong Ying, et al, U.S. application Ser. No. 10/853,942, filed on May 26, 2004.

"Method of and system for destreaking the photoelectric image in multi-energy computed tomography," invented by Zhengrong Ying, et al, U.S. application Ser. No. 10/860,984, filed on Jun. 4, 2004.

"Method of and system for extracting 3D bag images from continuously reconstructed 2D image slices in computed tomography," invented by Zhengrong Ying, et al, U.S. application Ser. No. 10/864,619, filed on Jun 9, 2004.

FIELD OF THE DISCLOSURE

The present disclosure relates to systems and methods for processing projection data in a computed tomography scanner, and more particularly to a method of and a system for correcting the measurements of CT number and atomic number of scanned materials due to the spectral variations in multi-energy computed tomography scanners.

BACKGROUND OF THE DISCLOSURE

Various X-ray baggage scanning systems are known for detecting the presence of explosives and other prohibited items in baggage, or luggage, prior to loading the baggage onto a commercial aircraft. A common technique of measuring a material's density is to expose the material to X-rays and to measure the amount of radiation absorbed by the material, the absorption being indicative of the density. Since many explosive materials may be characterized by a range of densities differentiable from that of other items typically found in baggage, explosives are generally amenable to detection by X-ray equipment.

Most X-ray baggage scanning systems in use today are of the "line scanner" type and include a stationary X-ray source, a stationary linear detector array, and a conveyor belt for transporting baggage between the source and detector array as the baggage passes through the scanner. The X-ray source generates an X-ray beam that passes through and is partially attenuated by the baggage and is then received by the detector array. During each measuring interval the detector array generates data representative of the integral of density of the planar segment of the baggage through which the X-ray beam passes, and this data is used to form one or more raster lines of a two-dimensional image. As the conveyor belt transports the baggage past the stationary source and detector array, the scanner generates a two-dimensional image representative of the density of the baggage, as viewed by the stationary detector array. The density image is typically displayed for analysis by a human operator.

Techniques using dual energy X-ray sources are known for providing additional information about a material's characteristics, beyond solely a density measurement. Techniques using dual energy X-ray sources involve measuring the X-ray absorption characteristics of a material for two different energy levels of X-rays. Depending upon the calibration of the scanner, dual energy measurements provide an indication of dual parameters of the material being scanned. For example, at one calibration setting, the dual parameters can be chosen to be the material's effective atomic number (Z is denoted as "effective atomic number") and the material's density. At another calibration setting, the dual parameters can be chosen to be the material's Photoelectric coefficients and the material's Compton coefficients. At yet another calibration setting, the dual parameters can be chosen to be an amount of a first material present (e.g., plastic) and an amount of a second material present (e.g., aluminum). Dual energy X-ray techniques for energy-selective reconstruction of X-ray Computer Tomography (hereinafter referred to as CT) images are described, for example, in Robert E. Alvarez and Albert Macovski, "Energy-selective Reconstructions in X-ray Computerized Tomography," Phys. Med. Biol. 1976, Vol. 21, No. 5, 733–744; and U.S. Pat. Nos. 4,029,963 and 5,132,998. One algorithm used to generate such dual parameters from dual energy X-ray projection data is known as the Alvarez/Macovski Algorithm (hereinafter referred to as AMA). Others are known in the art.

One proposed use for such dual energy techniques has been in connection with a baggage scanner for detecting the presence of explosives in baggage. Explosive materials are generally characterized by a known range of atomic numbers and are therefore amenable to detection by such dual energy X-ray sources. One such dual energy source is described in U.S. Pat. No. 5,661,774, entitled "Improved Dual Energy Power Supply," assigned to the present assignee and incorporated by reference. Other dual energy sources are known in the art.

Most explosives capable of significantly damaging an aircraft are sufficiently large in length, width, and height so as to be readily detectable by an X-ray scanner system regardless of the explosive's orientation within the baggage. Plastic explosives, however, present a particular challenge to baggage scanning systems. Due to their moldable nature, plastic explosives may be formed into geometric shapes that are difficult to detect. A plastic explosive powerful enough to damage an aircraft may be formed into a relatively thin sheet that is extremely small in one dimension and is relatively large in the other two dimensions. The detection of plastic explosives may be difficult because it may be difficult to see the explosive material in the image, particularly when the material is disposed so that the thin sheet is parallel to the direction of the X-ray beam as the sheet passes through the system.

Thus, detection of suspected baggage requires very attentive operators. The requirement for such attentiveness can result in greater operator fatigue, and fatigue as well as any distractions can result in a suspected bag passing through the system undetected. Accordingly, a great deal of effort has been made to design a better baggage scanner. Such designs, for example, have been described in U.S. Pat. No. 4,759,047 (Donges et al.); U.S. Pat. No. 4,884,289 (Glockmann et al.); U.S. Pat. No. 5,132,988 (Tsutsui et al.); U.S. Pat. No. 5,182,764 (Peschmann et al.); U.S. Pat. No. 5,247,561 (Kotowski); U.S. Pat. No. 5,319,547 (Krug et al.); U.S. Pat. No. 5,367,552 (Peschmann et al.); U.S. Pat. No. 5,490,218 (Krug et al.) and German Offenlegungsschrift DE 31 503 06 A1 (Heimann GmbH).

At least one of these designs, described in U.S. Pat. No. 5,182,764 (Peschmann et al.) and U.S. Pat. No. 5,367,552 (Peschmann et al.) (hereinafter the '764 and '552 patents), has been commercially developed and is referred to hereinafter as the "Invision Machine." The Invision Machine includes a CT scanner of the third generation type, which typically includes an X-ray source and an X-ray detector system secured respectively to diametrically opposite sides of an annular-shaped platform or disk. The disk is rotatably mounted within a gantry support so that in operation the disk continuously rotates about a rotation axis while X-rays pass from the source through an object positioned within the opening of the disk to the detector system.

The detector system can include a linear array of detectors disposed as a single row in the shape of a circular arc having a center of curvature at the focal spot of the X-ray source, i.e., the point within the X-ray source from which the X-rays emanate. The X-ray source generates a fan shaped beam, or fan beam, of X-rays that emanates from the focal spot, passes through a planar imaging field, and is received by the detectors. The CT scanner includes a coordinate system defined by X-, Y- and Z-axes, wherein the axes intersect and are all normal to one another at the center of rotation of the disk as the disk rotates about the rotation axis. This center of rotation is commonly referred to as the "isocenter." The Z-axis is defined by the rotation axis and the X- and Y-axes are defined by and lie within the planar imaging field. The fan beam is thus defined as the volume of space defined between a point source, i.e., the focal spot, and the receiving surfaces of the detectors of the detector array exposed to the X-ray beam. Because the dimension of the receiving surfaces of the linear array of detectors is relatively small in the Z-axis direction the fan beam is designed to be relatively thin in the Z-axis direction. Each detector generates an output signal representative of the intensity of the X-rays incident on that detector. Since the X-rays are partially attenuated by all the mass in their path, the output signal generated by each detector is representative of the density of all the mass disposed in the imaging field between the X-ray source and that detector.

As the disk rotates, the detector array is periodically sampled, and for each measuring interval each of the detectors in the detector array generates an output signal representative of the density of a portion of the object being scanned during that interval. The collection of all of the output signals generated by all the detectors in a single row of the detector array for any measuring interval is referred to as a "projection," or equivalently as a "view," and the angular orientation of the disk (and the corresponding angular orientations of the X-ray source and the detector array) during generation of a projection is referred to as the "projection angle." At each projection angle, the path of the X-rays from the focal spot to each detector, called a "ray," increases in cross section from an appropriate point source to the receiving surface area of the detector, and thus is thought to magnify the density measurement because the receiving surface area of the detector area is larger than any cross sectional area of the object through which the ray passes.

As the disk rotates around the object being scanned, the scanner generates a plurality of projections at a corresponding plurality of projection angles. Using well-known algorithms, a CT image of the object may be generated from all the projection data collected at each of the projection angles. The CT image is representative of the density of a two dimensional "slice" of the object through which the fan beam has passed during the rotation of the disk through the various projection angles. The resolution of the CT image is determined in part by the width of the receiving surface area of each detector in the plane of the fan beam, the width of the detector being defined herein as the dimension measured in the same direction as the width of the fan beam, while the length of the detector is defined herein as the dimension measured in a direction normal to the fan beam parallel to the rotation or Z-axis of the scanner. In general, the resolution of the CT image is inversely proportional to the width of the receiving surface of each detector in the plane of the fan beam.

Referring to the drawings, FIGS. 1, 2 and 3 show perspective, end cross-sectional and radial cross-sectional views, respectively, of a typical baggage scanning system 100, which includes a conveyor system 110 for continuously conveying baggage or luggage 112 in a direction indicated by arrow 114 through a central aperture of a CT scanning system 120. The conveyor system includes motor driven belts for supporting the baggage. Conveyer system 110 is illustrated as including a plurality of individual conveyor sections 122; however, other forms of conveyor systems may be used.

The CT scanning system 120 includes an annular shaped rotating platform, or disk, 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism, such as the one described in U.S. Pat. No. 5,473,657 issued Dec. 5, 1995 to Gilbert McKenna, entitled "X-ray Tomographic Scanning System," which is assigned to the present assignee and, which is incorporated herein in its entirety by reference. Rotating platform 124 defines a central aperture 126 through which conveyor system 110 transports the baggage 112.

The system 120 includes an X-ray tube 128 and a detector array 130 which are disposed on diametrically opposite sides of the platform 124. The detector array 130 is preferably a two-dimensional array, such as the array described in U.S. Pat. No. 6,091,795 entitled, "Area Detector Array for Computed Tomography Scanning System." Other suitable arrays are known in the art. The system 120 further includes a data acquisition system (DAS) 134 for receiving and processing signals generated by detector array 130, and an X-ray tube control system 136 for supplying power to, and otherwise controlling the operation of, X-ray tube 128. The system 120 is also preferably provided with a computerized system (not shown) for processing the output of the data acquisition system 134 and for generating the necessary signals for operating and controlling the system 120. The computerized system can also include a monitor for displaying information including generated images. System 120 also includes shields 138, which may be fabricated from lead, for example, for preventing radiation from propagating beyond gantry 125.

The X-ray tube 128 may generate a pyramidally shaped beam, often referred to as a "cone beam," 132 of X-rays that pass through a three dimensional imaging field, through which conveying system 110 transports baggage 112. After passing through the baggage disposed in the imaging field, detector array 130 receives cone beam 132 and generates signals representative of the densities of exposed portions of baggage 112. The beam therefore defines a scanning volume of space. Platform 124 rotates about its rotation axis 127, thereby transporting X-ray source 128 and detector array 130 in circular trajectories about baggage 112 as the conveyor system 110 continuously transports baggage through central aperture 126, so as to generate a plurality of projections at a corresponding plurality of projection angles. When dual energy scanning mode is configured, the control system 136 supplies modulated high voltages with respect to alternating projection angles to the X-ray tube 128. The detector array 130 then receives data corresponding to high-energy and low-energy X-ray spectra in alternating projection angles.

Post-reconstruction analysis and pre-reconstruction analysis are the two prior art techniques generally recognized for using dual energy X-ray sources in materials analysis (e.g., in a baggage scanner for detecting the presence of explosives in baggage). In post-reconstruction analysis, the signal flow is as shown in FIG. 4. The scanner 120 is typically similar to the one shown in FIGS. 1–3 and has an X-ray source capable of producing a fan or cone beam at two distinct energy levels (i.e., dual energy). The DAS 134 gathers signals generated by detector array 130 at discrete angular positions of the rotating platform 124, and passes the signals to the pre-processing unit 206. The pre-processing unit 206 re-sorts the data it receives from the DAS 134 in order to optimize the sequence for the subsequent mathematical processing. The pre-processing unit 206 also corrects the data from the DAS 134 for detector temperature, intensity of the primary beam, gain and offset, and other deterministic errors. Finally, the pre-processing unit 206 extracts data corresponding to high-energy views and routes it to a high-energy path 208, and routes the data corresponding to low-energy views to a low-energy path 210. A first reconstruction computer 218 receives the projection data from the high-energy path 208 and generates a CT image $I_H$ 226 corresponding to the high-energy series of projections. A second reconstruction computer 220 receives the projection data from the low-energy path 210 and generates a CT image $I_L$ 224 corresponding to the low-energy series of projections. A post-processing unit 230 receives the high-energy CT image 226 and the low-energy CT image 224 and performs voxel-by-voxel processing to yield the effective atomic number (Z is denoted as effective atomic number) image $I_z$ 232. The Z image 232 and the high-energy CT image 226 can be provided to operators on a display 240, and both images can be used for automatic explosive detection in 238 as well. The images from the post-reconstruction analysis usually do not yield accurate estimates of the material's effective atomic number, and suffer low SNR (Signal to Noise Ratio) and many artifacts as well.

In pre-reconstruction analysis, the signal flow is as shown in FIG. 5. As is described herein for pre-reconstruction analysis, the dual energy decomposition computer 212 receives the projection data on the high-energy path 208 and the low-energy path 210 and performs the Alvarez/Macovski Algorithm to produce a first stream of projection data $A_c$ 214, which is dependent on a first parameter of the material being scanned, and a second stream of projection data $A_p$ 216, which is dependent on a second parameter of the material scanned. The first material parameter is often the Compton coefficient $a_c$, and the second material parameter is often the photoelectric coefficient $a_p$. A first reconstruction computer 219 receives the first stream of projection data 214 and generates a Compton image $I_c$ 227 from the series of projections corresponding to the first material parameter. A second reconstruction computer 221 receives the second stream of projection data 216 and generates a photoelectric image $I_p$ 225 from the series projections corresponding to the second material parameter. The third reconstruction computer 218 receives the stream of projection data 208 and generates a high-energy CT image $I_H$ 226. The two images 225 and 227 are processed in the post-processing unit 230 to yield a Z image $I_z$ 232. The High-energy CT image 226 and the Z image 232 can be provided to operators on a display 240, and both images can be used for automatic explosive detection in detection unit 238 as well. The pre-reconstruction analysis yields better estimates of material's effective atomic number than the post-reconstruction analysis. However the pre-reconstruction analysis requires one more reconstruction computer than the post-reconstruction analysis.

Various approaches have been used for decomposition of the input projection data $P_L$ and $P_H$ into Compton projections $A_c$ and photoelectric projections $A_p$. For example, the AMA method approximates $P_L$ and $P_H$ using polynomial functions in terms of $A_c$ and $A_p$. The coefficients of the polynomial functions are determined through a calibration procedure as follows. By measuring the projection values of the combination of various thicknesses of two known materials, the coefficients can be calculated through a polynomial least squares fitting between the measured and modeled $P_L$ and $P_H$. Once the coefficients of the polynomial functions are determined, the decomposition of the Compton and Photoelectric projections $A_c$ and $A_p$ from projections $P_L$ and $P_H$ is usually solved using the Newton-Raphson method.

Another prior art method of performing decomposition is the direct approximation method, discussed in L. A. Lehmann, R. E. Alvarez, A. Macovski, W. R. Brody, N. J. Pelc, S. J. Riederer, and A. L. Hall, *Generalized Image Combinations In Dual KVP Digital Radiography*, Med. Phys. 8, 659–667 (1981). In the direct approximation method, $A_c$ and $A_p$ are approximated as polynomial functions in terms of $P_L$ and $P_H$. The coefficients of the polynomial functions in the direct approximation method are determined through a calibration procedure by measuring the projection values of the combination of various thicknesses of two known materials.

In yet another prior art method, decomposition is accomplished using iso-transmission lines, described K. Chuang and H. K. Huang, *A Fast Dual-Energy Computational Method Using Isotransmission Lines and Tables*, Med. Phys. 14, 186–192 (1987). According to this method, for a given projection value, an iso-transmission line is represented by a linear equation in two basis functions. The iso-transmission line method requires a large amount of calibration data. Further, the iso-transmission line becomes increasingly nonlinear as the projection value increases. In such a situation, the linear equations are not valid and the method causes large approximation errors.

CT images and Z (effective atomic number) images can be generated from both the pre-reconstruction and post-reconstruction analysis. The CT images measure the CT number of scanned materials, which approximates the density of the materials; and the Z image measures the effective atomic number of the scanned materials. The measurements of CT number and Z are used for automatic explosive detection. However the measurements vary over time on a scanner due to HVPS (High Voltage Power System) drifts and vary across scanners due to the components variations in the x-ray beam lines. Such measurement variations interfere with the automatic detection of explosives, resulting in a degraded detection rate and/or an increased false alarm rate. The HVPS drifts cause the voltages applied to the X-ray tube to change over time, resulting in the change of X-ray spectra over time. The component variations in the X-ray beam line of scanners also produce different X-ray spectra on different scanners. Therefore it is necessary to have an algorithm to correct the measurement variations due to the X-ray spectral variations, so that any fixed material yields substantially the same measurement values at any time at any scanner.

SUMMARY OF THE DISCLOSURE

In accordance with one aspect of the disclosure, a spectral correction algorithm in multi-energy X-ray computed tomography is provided to correct reconstructed images, such as high-energy CT images and Z images, for spectral variations, which include (1) time variations on a scanner due to HVPS drift and (2) scanner to scanner variations due to the beamline component differences. In one embodiment of the disclosure, the spectral correction algorithm uses a copper filter mounted on the detector array for tracking the spectral changes. In another embodiment of the disclosure, an offline spectral calibration is provided to generate necessary parameters for the online correction algorithm.

In accordance with one aspect of the disclosure, the high-energy copper ratio and low-energy copper ratio are computed. The computation of copper ratios includes a step of correcting detector readings for the offset values. The computation of copper ratios also includes averaging the offset corrected detector readings over the detectors shielded by the copper filter (copper counts) and over the nearby detectors without the copper filter's shielding (air counts). In one embodiment, the copper counts and air counts are also averaged over multiple views corresponding to X-ray beam paths underneath the conveyor belt. The copper ratios are the ratios of the averaged air counts to the averaged copper counts. The copper ratios include base copper ratios generated during the offline spectral calibration, and working copper ratios generated during the online spectral correction.

In accordance with one aspect of the disclosure, the working copper ratios are used to generate working air tables. The working air tables are computed using base air tables obtained during the offline spectral calibration procedure and changes predicted by the working copper ratios. The differences between the working copper ratios and the base copper ratios are computed for predicting the changes in the air tables, which are calculated as linear combinations of the differences of copper ratios. The coefficients used in the linear combinations are obtained from the offline spectral calibration procedure. Higher order (than linear) combinations of the differences of copper ratios can also be used to predict the changes in the air tables. In another embodiment, base air tables can also be obtained using an air calibration as described in the assignee's U.S. Pat. No. 5,949,842 (David Schafer et al), incorporated herein by reference. In an alternative embodiment, the step of generating working air tables can be skipped, that is, air tables generated from the air calibration procedure mentioned previously, or the base air tables generated during the offline spectral calibration can be used.

In one embodiment, the working copper ratios are also used to generate scales and offsets for correcting reconstructed images, including high-energy CT images and Z images, for spectral variations. The offsets include one of three materials' working CT numbers and one of three materials' working effective atomic numbers, which are computed using materials' base CT numbers and base effective atomic numbers obtained during the offline spectral calibration. The differences between the working copper ratios and the base copper ratios are used for predicting the changes of the materials' CT numbers and effective atomic numbers, which are calculated as linear combinations of the differences of copper ratios. The coefficients used in the linear combinations are obtained from the offline spectral calibration procedure. Higher order (than linear) combinations of the differences of copper ratios can also be used to predict the changes of the materials' CT numbers and effective atomic numbers. In another embodiment, the calculated materials' working CT numbers and working effective atomic numbers are used to calculate scales for correction.

In accordance with one aspect of the disclosure, the computed scales and offsets are used to correct reconstructed images, including high-energy CT images and Z images, on a voxel-by-voxel basis. The corrections can also include crossover terms between high-energy CT images and Z images.

In one embodiment, an offline spectral calibration procedure is also provided to generate necessary parameters for correction. The calibration procedure uses an IQP (Image Quality Phantom), which contains at least three materials: for example, PVC (Poly-Vinyl Chloride), Teflon, and Nylon. Other and/or additional materials can also be used for calibration.

In accordance with one aspect of the disclosure, the parameters generated in the offline spectral calibration include base copper ratios, base air tables, air coefficients, three materials' base CT numbers and base effective atomic numbers, and three sets of materials' dependent coefficients. In accordance with another aspect of the disclosure, the offline calibration procedure includes at least three air scans and three IQP scans. At least three materials inside the IQP are used as reference for calibration and correction, so that at any time any scanner produces the same CT numbers and effective atomic numbers for each of the three materials. Three or more individual materials not contained in the IQP can also be used for calibration and correction, and each of them is also scanned at least three times.

A system for correcting reconstructed images, including high-energy CT images and Z images, for spectral variation using copper ratios is also disclosed. The system includes modules configured to implement the above functionality. The system may include a copper filter mounted on the detector array, a module for calculating copper ratios, a module for generating working air tables, a module for computing scales and offsets, and a module for correcting reconstructed images, including high-energy CT images and Z images, using the computed scales and offsets. The system may also include a module for performing the offline spectral calibration as described above.

While this disclosure has been particularly shown and described with references to preferred embodiments thereof, it will be understood by those skilled in the art that various changes in form and details may be made therein without departing from the spirit and scope of the disclosure as defined by the following claims.

BRIEF DESCRIPTION OF THE DRAWINGS

The drawing figures depict preferred embodiments by way of example, not by way of limitations. In the figures, like reference numerals refer to the same or similar elements.

DETAILED DESCRIPTION OF THE PREFERRED EMBODIMENTS

I. Overview

Figure 6:
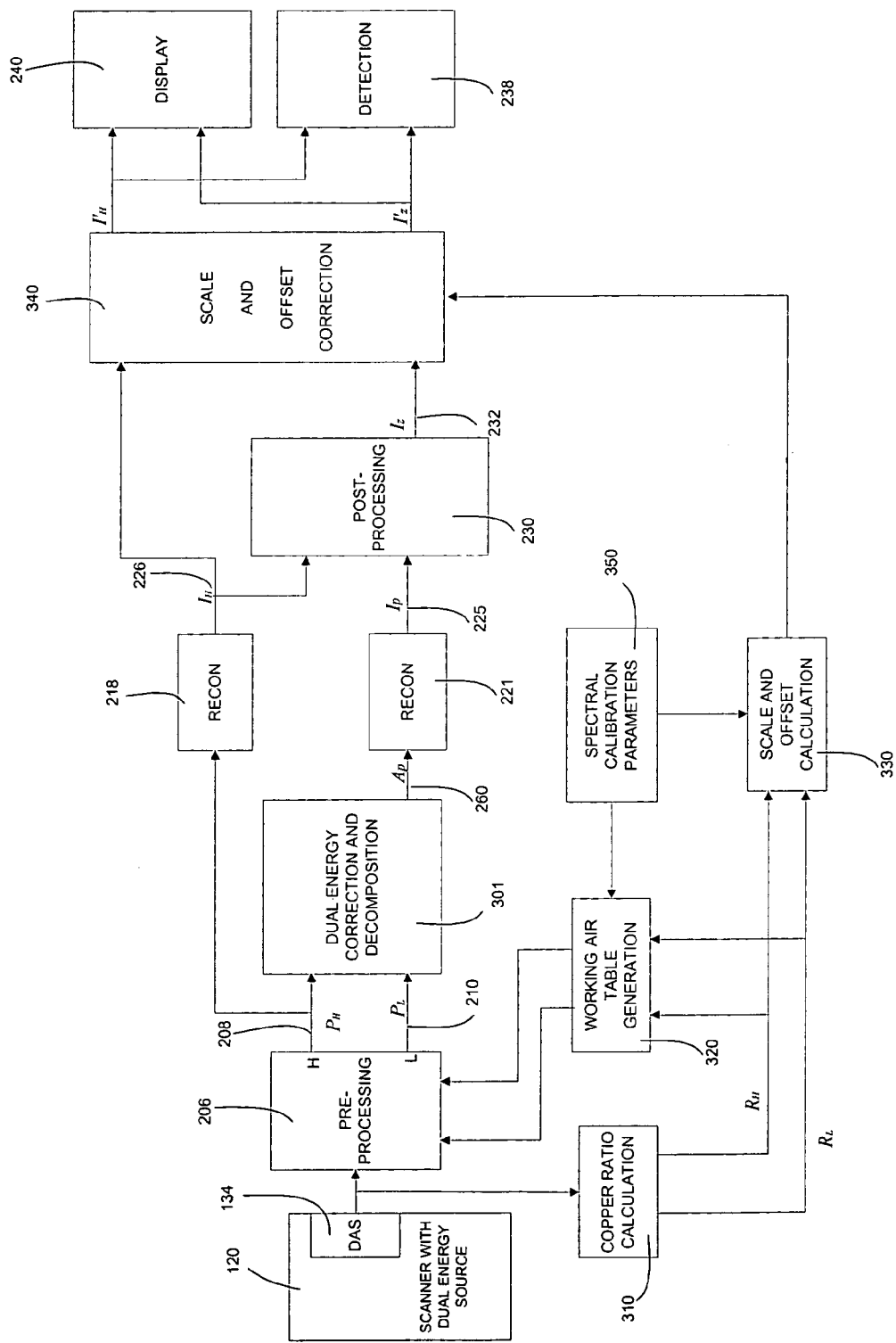
FIG. 6 is a signal flow diagram of a system of the present disclosure.

FIG. 6 illustrates an embodiment of a signal and data flow of the scanner system for explosive detection for the checked baggage for an airport arranged to carry out the process of the present disclosure. The scanner 120 is typically similar to the one shown in FIG. 1, modified in accordance with the teachings of the present disclosure. Scanner 120 comprises an X-ray source capable of producing a cone beam at two distinct energy levels (i.e., dual energy) at alternating view angles. Each rotation of the disk, the detectors collect a total of $V_{one}$ views of data. The view angle index v ranges from 0 to $V_{one}-1$ for the $V_{one}$ views. For purposes of exposition, the odd number view index corresponds to low-energy X-ray spectrum, and the even number view index corresponds to high-energy X-ray spectrum. The two energy levels are determined by the DC (Direct Current) and AC (Alternating Current) voltage supplied by the HVPS (High Voltage Power Supply) to the X-ray tube. The HVPS produces the following voltage, $$V = V_{DC} + V_{AC} \sin(2\pi ft)$$

wherein $V_{DC}$ is the DC voltage, $V_{AC}$ is the AC voltage, and f is the frequency of the AC voltage, the latter being equal to the product of the disk rotational speed and number of views per rotation. The DC voltage and AC voltage are optimally chosen so that the reconstructed Z image yields the highest SNR (Signal to Noise Ratio). For example, in the assignee's commercial scanner system similar to the one shown in connection with FIGS. 1–3, the DC voltage is set to 140 kV, and the AC voltage is set to 40 kV. However, the HVPS drifts in both DC and AC voltages when in operation, resulting in variations of measured CT numbers and effective atomic numbers of scanned materials. While the embodiment of FIG. 6 is described herein as including functional units for ease of exposition, it should be understood that some or all of the functionality described can be carried out with software running on one or more computer processors.

Figure 7:
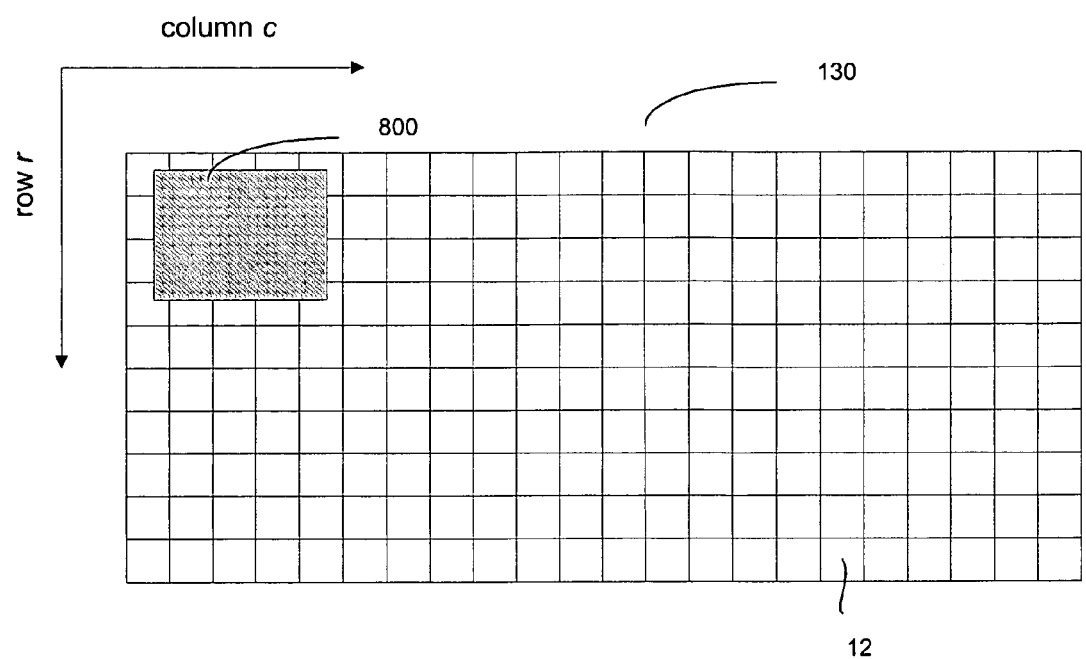
FIG. 7 illustrates a detector array with a copper filter of the present disclosure.
Figure 8:
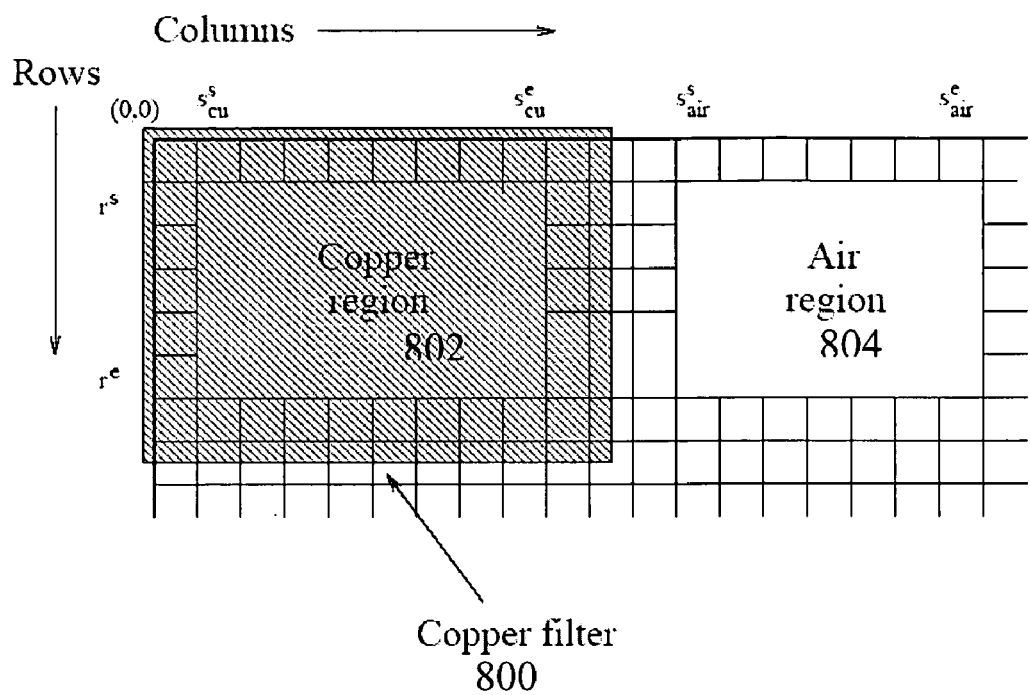
FIG. 8 illustrates the row indices and column indices of the detectors used for computing copper ratios of the present disclosure.

FIG. 7 shows a detector array 130 comprising a two-dimensional matrix of detectors, each individual detector being denoted at 12. A rectangular copper filter 800, for example, (69 mm long, 22 mm wide, 0.43 mm thick) is mounted on a portion of the two-dimensional array, e.g., over the upper left corner of the two-dimensional detector array. Thus, as shown in FIG. 8, some of the detectors 802 are shielded by the copper filter, and others of the detectors 804 are not shielded by the copper filter. The starting row index of detectors 802 is indicated as $r^s$, the ending row index is indicated as $r^e$, the starting column index is indicated as $s_{cu}^s$, and the ending column index is indicated as $s_{cu}^e$. For the detectors 804, the starting and ending row indices are the same as the detectors 802; the starting column index is indicated as $s_{air}^s$, and the ending column index is indicated as $s_{air}^e$.

The filter is preferably mounted on detectors where received data is not required to be used for image reconstruction during a scan, i.e., one location is in the upper left corner of the whole detector array. More specifically, data are preferably reconstructed using the Nutating Slice Reconstruction algorithm as described in the assignee's U.S. Pat. No. 5,802,134 (Greg Larson et al.), the algorithm does not require data from the upper left corner of the array for reconstruction. Therefore, the placement of the copper filter in the upper left corner does not affect the quality of the reconstructed images.

Figure 9:
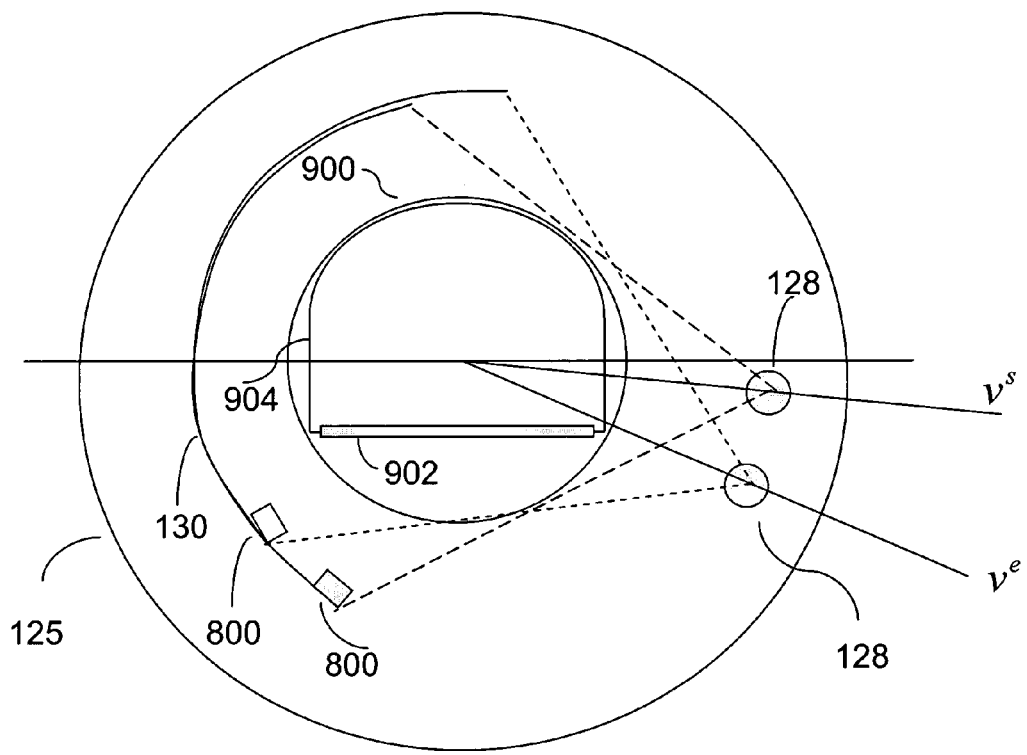
FIG. 9 illustrates the starting view angle and ending view angle for computing copper ratios of the present disclosure.

FIG. 9 illustrates the range of view angles at which the detectors shielded by the copper filter receive X-ray beams not blocked by the conveyor belt 902. In FIG. 9, 900 is a reconstruction circle, and 904 is the scanner tunnel. The range of the view angles is determined by a starting view angle $v^s$ and an ending view angle $v^e$.

The detectors under the copper filter receive different X-ray spectra than those not shielded by the copper filter. The ratios of the averaged X-ray intensity received by the copper shielded detectors to the averaged X-ray intensity received by the detectors without copper filter shielding are called copper ratios. In accordance with one aspect of the disclosure, the copper ratios are used to track the change of X-ray spectra of a scanner.

Referring again to FIG. 6, the DAS 134 of scanner 120 gathers signals generated by detector array 130 (not shown in FIG. 6, but shown in FIG. 7) at discrete view angles of the rotating platform 124 (as, for example, illustrated in FIG. 8), and passes the signals to the pre-processing unit 206 and unit 310 for calculating the copper ratios. The copper ratios corresponding to the high-energy X-ray spectra and low-energy X-ray spectra are both preferably computed in unit 310. The calculated copper ratios together with the spectral calibration parameters obtained during an offline spectral calibration are used to generate working air tables, which in turn are used in the pre-processing unit 206 to generate low-energy and high-energy projections.

The pre-processing unit 206 preferably re-sorts the data it receives from the DAS 134 in order to optimize the sequence for the subsequent mathematical processing. The pre-processing unit 206 also preferably corrects the data from the DAS 134 for detector temperature, intensity of the primary beam, gain and offset, and other deterministic error factors. Finally, the pre-processing unit 206 preferably (1) extracts data corresponding to high-energy views and routes it to a high-energy path 208, and (2) extracts data corresponding to low-energy views and routes this data to a low-energy path 210.

The dual energy correction and decomposition unit 301 receives the projection data on the high-energy path 208 and the low-energy path 210 and performs a series of corrections and decomposition. The corrections include adaptive scatter correction described the assignee's "Method of and system for adaptive scatter correction in multi-energy computed tomography" by Zhengrong Ying, et al. U.S. application Ser. No. 10/853,942, filed on May 26, 2004 incorporated herein by reference; and destreaking the photoelectric image described in the assignee's "Method of and system for destreaking the photoelectric image in multi-energy computed tomography" by Zhengrong Ying, et. al. U.S. application Ser. No. 10/860,984, filed on Jun 4, 2004; incorporated herein by reference. Dual energy decomposition methods are described in the assignee's "Decomposition of Multi-Energy Scan Projections using Multi-Step Fitting" by Naidu, et. al. U.S. application Ser. No. 10/611,572, filed on Jul. 1, 2003, incorporated herein by reference; and "Method of and system for computing effective atomic number image in multi-energy computed tomography" by Zhengrong Ying, et. al. U.S. application Ser. No. 10/850,910, filed on May 21, 2004 incorporated herein by reference.

The dual energy correction and decomposition unit 301 preferably produces photoelectric projections 260 for reconstruction. A first reconstruction computer 221 receives the stream of the photoelectric projection data 260 and generates a photoelectric image $I_p$ 225. The second reconstruction computer 218 receives the stream of projection data 208 and generates a high-energy CT image $I_H$ 226. These two images 225 and 226 are processed in the post-processing unit 230 to yield a Z image $I_z$ 232.

The unit 340 preferably receives the high-energy CT image $I_H$ 226 and the Z image $I_z$ 232, and also the scales and offsets generated from the unit 330, to perform a correction on a voxel-by-voxel basis. The corrected high-energy CT image $I'_H$ and the Z image $I'_z$ can be displayed in unit 240, and can be used for automatic explosive detection in unit 238.

II. Spectral Correction

In accordance with the present disclosure, a preferred algorithm for correcting High-energy CT images and Z images for the spectral variations in multi-energy X-ray CT scanners is provided. The algorithm preferably comprises the following steps:

Generating copper ratios.
Computing working air tables.
Calculating scales and offsets.
Applying the scales and offsets to CT and Z images.

Figure 10:
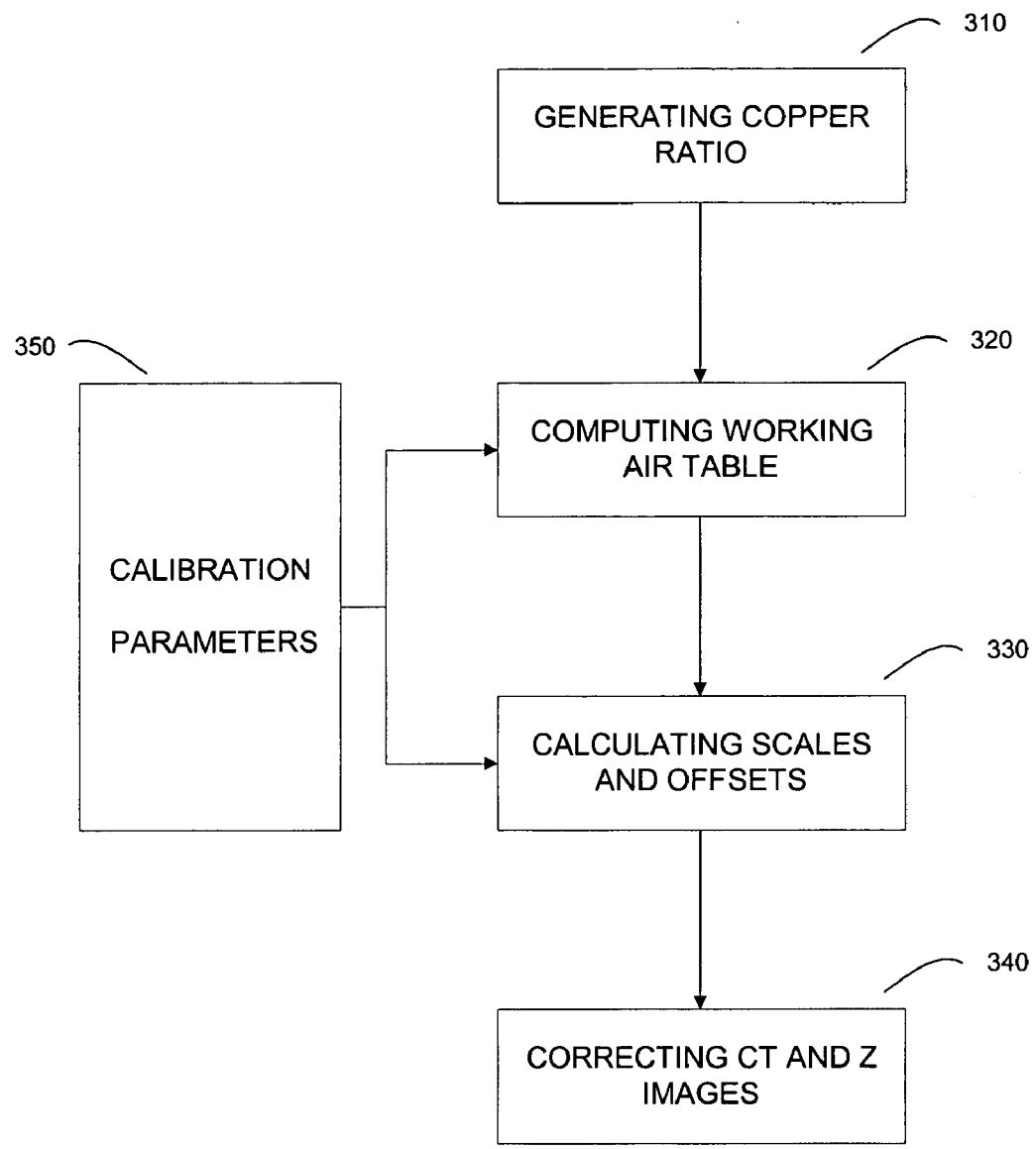
FIG. 10 contains a flow diagram which illustrates the logical flow of one embodiment of online spectral correction of the present disclosure.

FIG. 10 contains a flow chart of the correction algorithm, illustrating the above listed steps. In Step 310, copper ratios are calculated from the DAS outputs as follows. Denote $P_{off}$ (s, r) as the offset value of the detector s at row r of the two-dimensional detector array. The size of the two-dimensional detector array is R rows by S columns. As an example, in the assignee's commercial scanner system similar to the one illustrated in connection with FIGS. 1–3, R=24 and S=252. The offset table $P_{off}$(s, r) of all the detectors in the two-dimensional array is collected when the X-ray is turned off.

Still in Step 310, denote $P_{DAS}$ (v, s, r) as detector reading of the X-ray intensity value at detector s at row r of the two-dimensional detector array and at view v. An offset correction is performed as follows so that the detector readings correspond to zero when there are no X-rays, $$P_o(v,s,r)=P_{DAS}(v,s,r)-P_{off}(s,r)$$

where $P_o$ (v, s, r) is the offset corrected detector reading.

The offset corrected detector readings are then used to compute the average copper readings and average air readings. Denote $\overline{P}_{air}^h$ as the average high-energy air counts, $\overline{P}_{air}^l$ as the average low-energy air counts, $\overline{P}_{cu}^h$ as the average high-energy copper counts, $\overline{P}_{cu}^l$ as the average low-energy copper counts. $\overline{P}_{air}^h$, $\overline{P}_{air}^l$, $\overline{P}_{cu}^h$, and $\overline{P}_{cu}^l$ are computed as follows, $$\overline{P}_{air}^h = K_{air} \sum_{v \in \{v^s \le v \le v^e, \text{and } v \text{ is even}\}} \sum_{s=s_{air}^s}^{s_{air}^e} \sum_{r=r^s}^{r^e} P_o(v, s, r)$$

$$\overline{P}_{air}^l = K_{air} \sum_{v \in \{v^s \le v \le v^e, \text{and } v \text{ is odd}\}} \sum_{s=s_{air}^s}^{s_{air}^e} \sum_{r=r^s}^{r^e} P_o(v, s, r)$$

$$\overline{P}_{cu}^h = K_{cu} \sum_{v \in \{v^s \le v \le v^e, \text{and } v \text{ is even}\}} \sum_{s=s_{air}^s}^{s_{air}^e} \sum_{r=r^s}^{r^e} P_o(v, s, r)$$

$$\overline{P}_{cu}^l = K_{cu} \sum_{v \in \{v^s \le v \le v^e, \text{and } v \text{ is odd}\}} \sum_{s=s_{air}^s}^{s_{air}^e} \sum_{r=r^s}^{r^e} P_o(v, s, r)$$

where $K_{air}$ and $K_{cu}$ are computed as follows, $$K_{air} = \frac{2}{(v^e - v^s + 1)(s_{air}^e - s_{air}^s + 1)(r^e - r^s + 1)}$$

$$K_{cu} = \frac{2}{(v^e - v^s + 1)(s_{cu}^e - s_{cu}^s + 1)(r^e - r^s + 1)}$$

Figure 1:
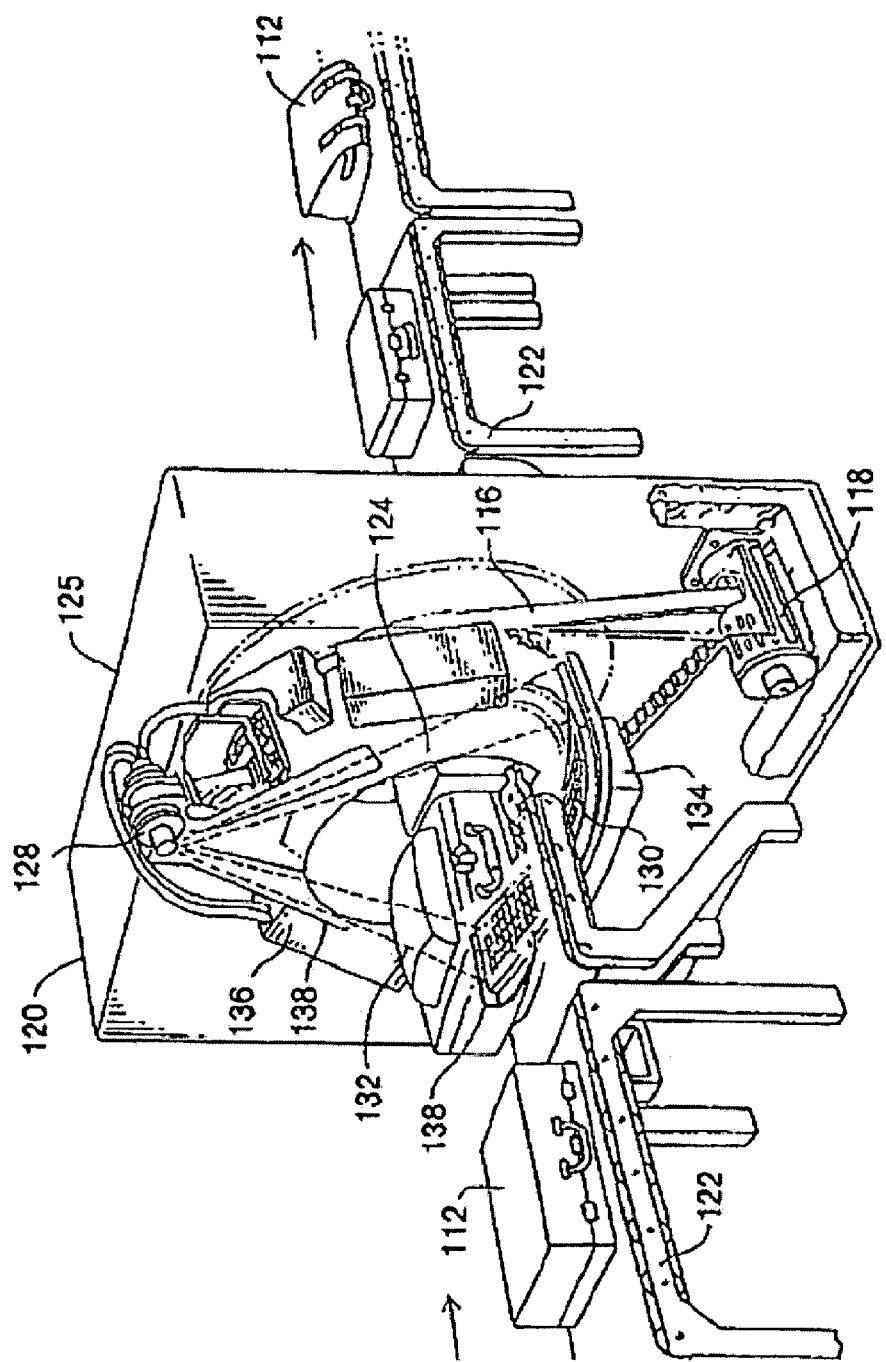
FIG. 1 is a perspective view of a baggage scanning system, known in the prior art.
Figure 2:
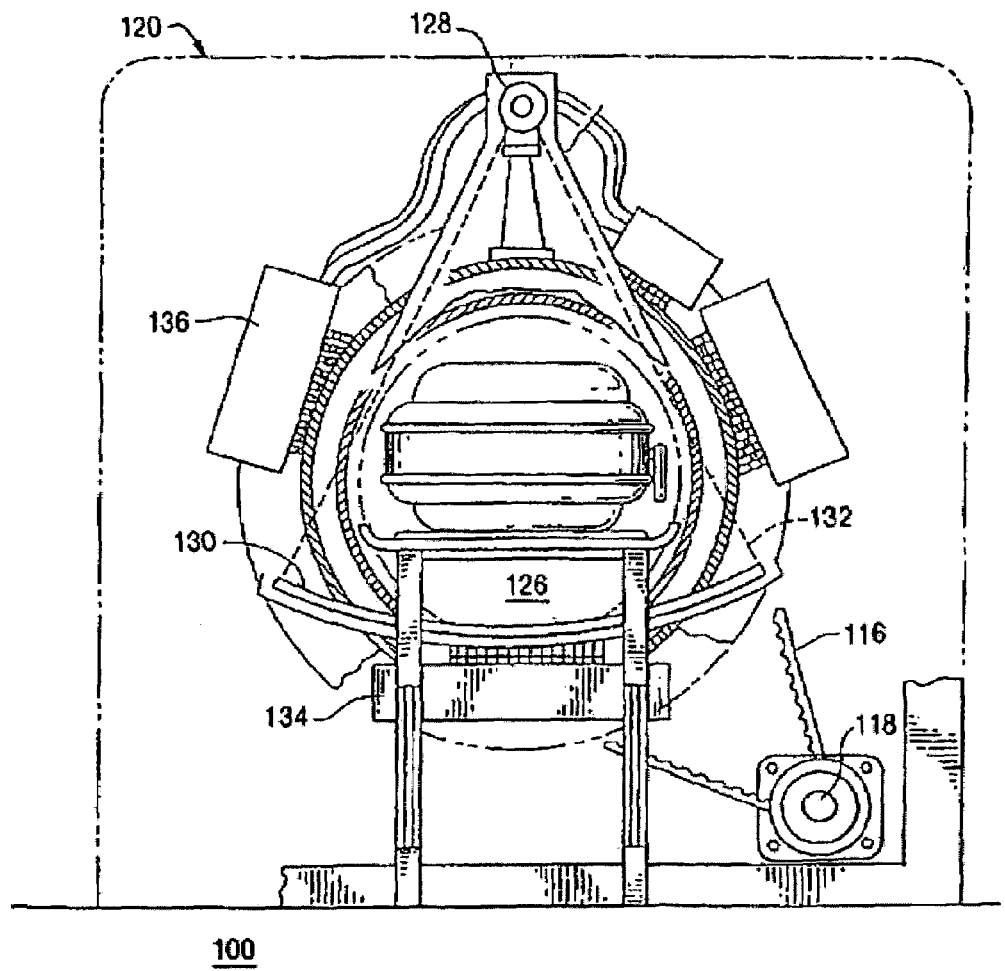
FIG. 2 is a cross-sectional end view of the system of FIG. 1.
Figure 3:
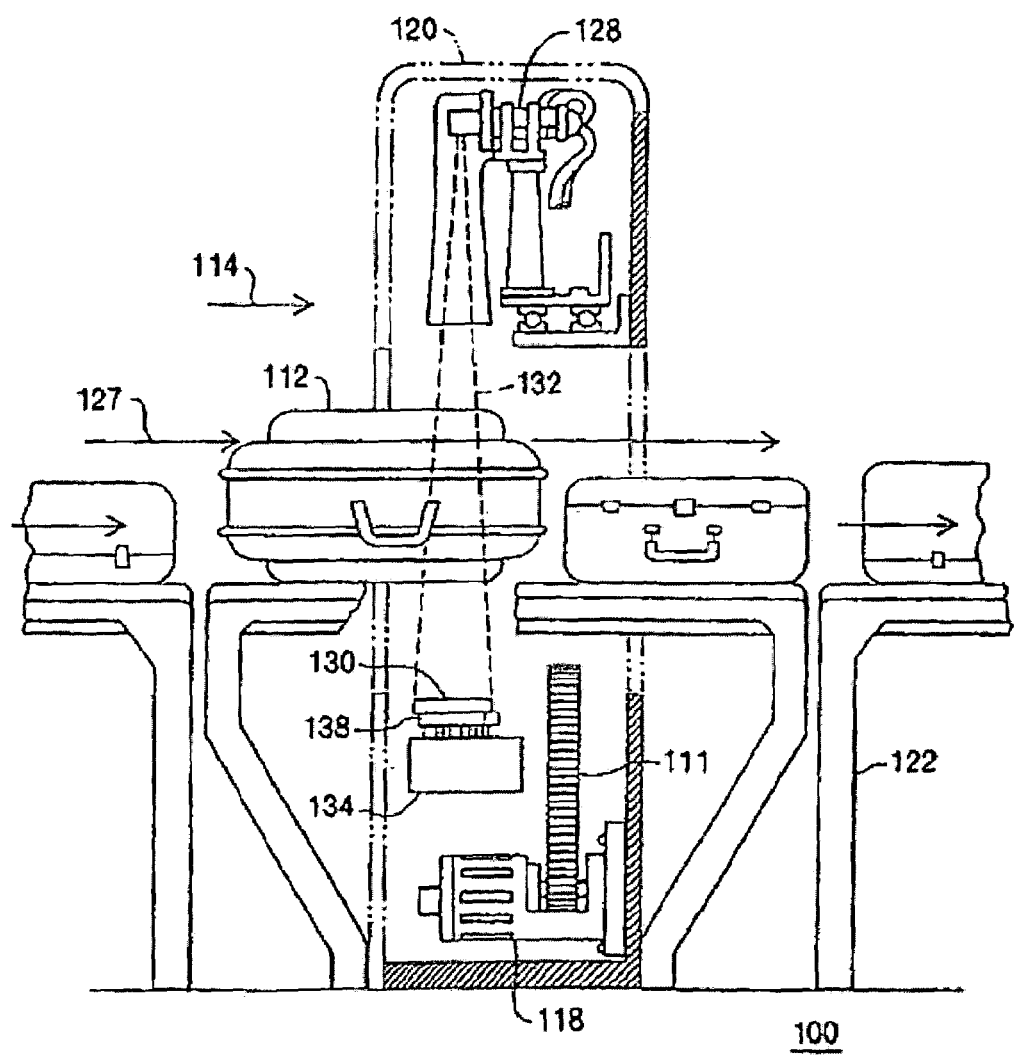
FIG. 3 is a cross-sectional radial view of the system of FIG. 1.
Figure 4:
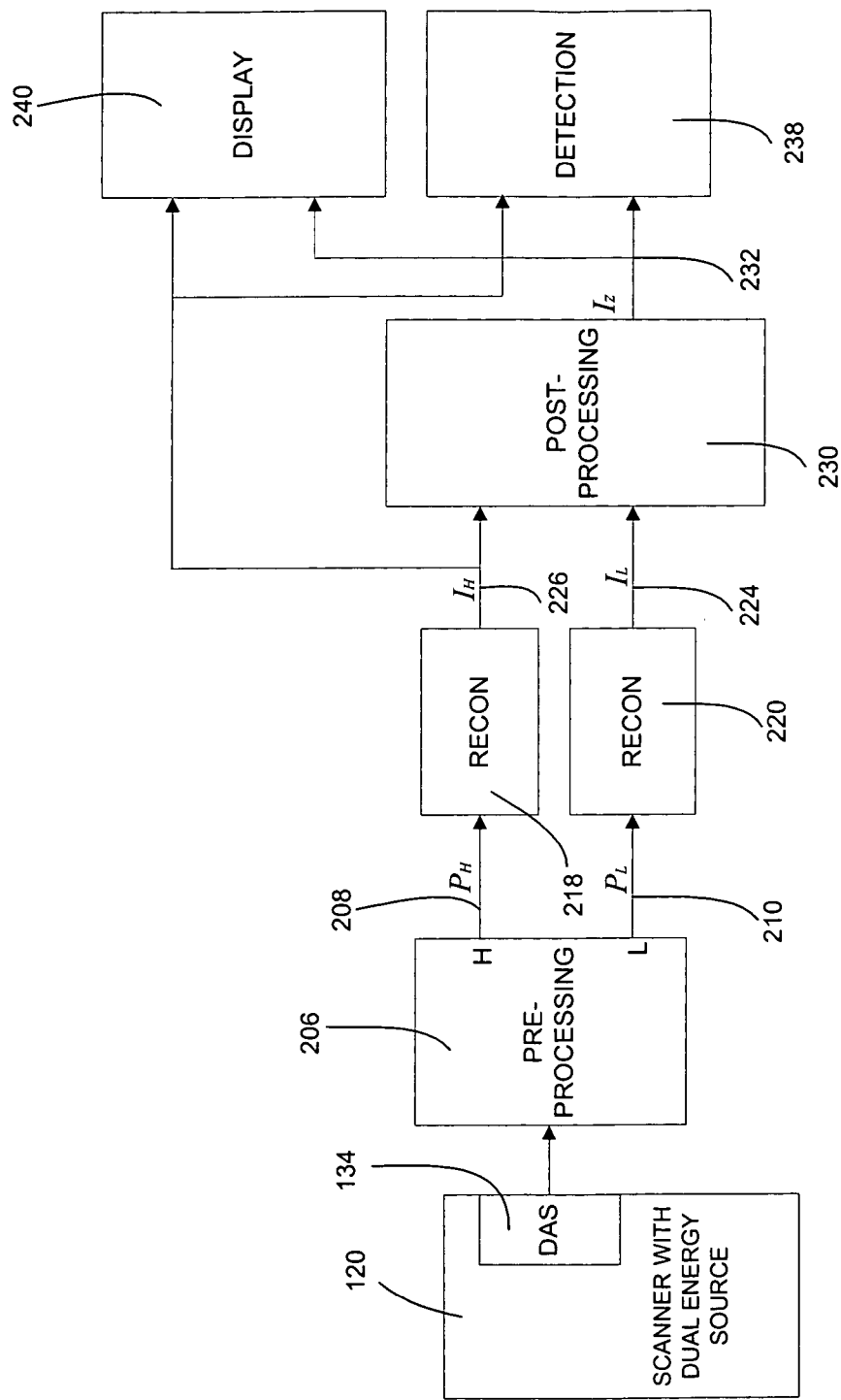
FIG. 4 is a signal flow diagram of a system capable of performing post-reconstruction analysis, useful in the system of FIG. 1.
Figure 5:
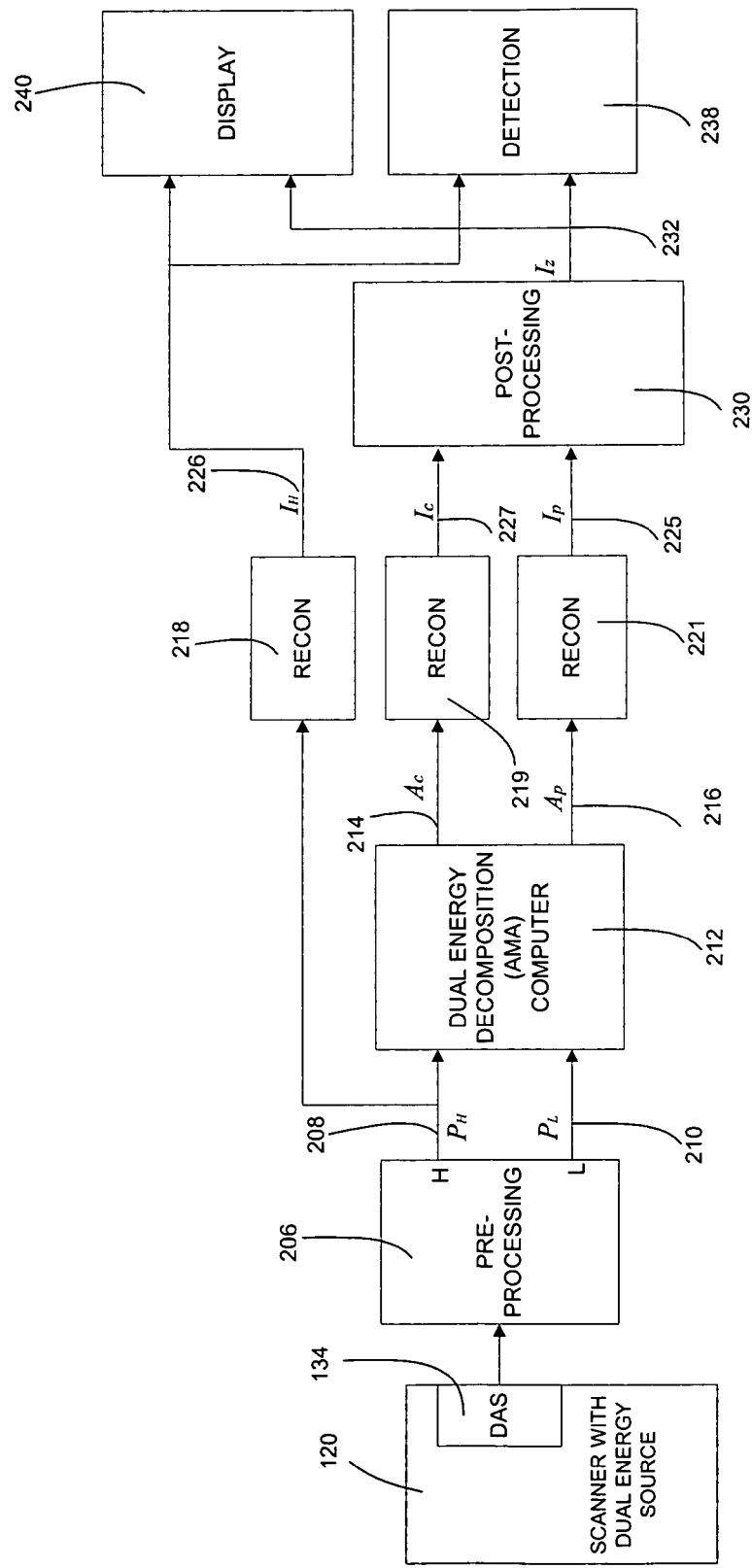
FIG. 5 is a signal flow diagram of a system capable of performing pre-reconstruction analysis, useful in the system of FIG. 1.

Note that the odd view angle v corresponds to the low-energy X-ray spectrum, and even view angle v corresponds to the high-energy X-ray spectrum as described in the scanner shown in FIGS. 1–3.

Still in Step 310, the averaged air counts and copper counts are used to calculate copper ratios. $R_h$ is denoted as high-energy copper ratio, and $R_l$ is denoted as low-energy copper ratio. $R_h$ and $R_l$ are calculated as follows, $$R_h = \frac{\overline{P}_{air}^h}{\overline{P}_{cu}^h} \quad \text{(a)}$$

$$R_l = \frac{\overline{P}_{air}^l}{\overline{P}_{cu}^l} \quad \text{(b)}$$

As discussed before, the copper ratios computed for the high-energy and low-energy X-ray spectra are fixed for a given beamline of a scanner, and a pair of the AC and DC voltages applied to the X-ray tube. Therefore, changes in the copper ratios reflect the changes in the X-ray spectra of a scanner.

The air tables are used in the pre-processing unit 206 to generate the corresponding high-energy and low-energy projections. Air tables are usually generated once a day before scanning any piece of baggage in the case of no HVPS drift. Due to the drift of the HVPS, air tables corresponding to the current X-ray spectra have to be generated to reflect the current X-ray spectra. However, air tables have to be generated in the absence of any object in the scanner. Therefore working air tables are generated based on base air tables collected during the offline spectral calibration and changes predicted by the current copper ratios.

In Step 320, working air tables for high-energy and low-energy data are computed as follows. Denote $A'_h (v, s, r)$ as the working air table for the high-energy X-ray spectrum, and $A'_l (v, s, r)$ as the working air table for the low-energy X-ray spectrum. Note that $v=0, \ldots, V-1$, $s=0, \ldots, S-1$, and $r=0, \ldots, R-1$. Denote $A_h^0(v, r, s)$ and base air table for the high-energy X-ray spectrum, and $A_l^0 (v, s, r)$ as the base air table for the low-energy X-ray spectrum. The base air tables are obtained during the offline spectral calibration in Step 350, which will be described in detail later. Denote $\Delta_h^A (v, s, r)$ and $\Delta_l^A (v, s, r)$ as the changes of the air counts due to the HVPS drift for high-energy spectrum and low-energy spectrum respectively. The working air tables are computed as follows, $$A'_h(v,s,r) = A_h^0(v,s,r) + \Delta_h^A(v,s,r)$$

$$A'_l(v,s,r) = A_l^0(v,s,r) + \Delta_l^A(v,s,r)$$

The changes of the air counts $\Delta_h^A (v, s, r)$ and $\Delta_l^A (v, s, r)$ are computed as follows, $$\Delta_h^A(v,s,r) = m_{h,h}^A(v,s,r)(R_h - R_h^0) + m_{h,l}^A(v,s,r)(R_l - R_l^0)$$

$$\Delta_l^A(v,s,r) = m_{L,h}^A(v,s,r)(R_h - R_h^0) + m_{l,l}^A(v,s,r)(R_l - R_l^0)$$

where $R_h$ and $R_l$ are the working copper ratios, $R_h^0$ and $R_l^0$ are the base copper ratios obtained during the offline spectral calibration in Step 350, $m_{h,h}^A (v, s, r)$, $m_{h,l}^A (v, s, r)$, $m^{l,h,A} (v, s, r)$, and $m_{l,l}^A (v, s, r)$ are air coefficients, which are also obtained during the offline spectral calibration in Step 350.

The working air tables are used in the pre-processing unit 206 to yield the high-energy and low-energy projections. The computation of the high-energy and low-energy projections, the dual energy decompositions and corrections, High-energy CT image and Z image reconstructions are described in the following filed assignee's co-pending patents: "Method of and system for adaptive scatter correction in multi-energy computed tomography" by Zhengrong Ying, et. al. U.S. application Ser. No. 10/853,942, filed on May 26, 2004 "Method of and system for destreaking the photoelectric image in multi-energy computed tomography" by Zhengrong Ying, et. al. U.S. application Ser. No. 10/860,984, filed on Jun. 4, 2004; "Decomposition of Multi-Energy Scan Projections using Multi-Step Fitting" by Naidu, et. al. U.S. application Ser. No. 10/611,572, filed on Jul. 1, 2003; and "Method of and system for computing effective atomic number image in multi-energy computed tomography" by Zhengrong Ying, et. al. U.S. application Ser. No. 10/850,910, filed on May 21, 2004. All of them are incorporated herein by reference.

Next in Step 330, scales and offsets for correcting the spectral variations are calculated according to the working copper ratios. The scales and offsets are generated using three materials as reference, so that at any time any scanner produces same CT numbers and effective atomic numbers for these three materials. The three materials are chosen (or specified) in the offline spectral calibration in Step 350. The scales generated in this step include $S_{H,H}$, $S_{H,Z}$, $S_{Z,H}$, and $s_{Z,Z}$; the offsets generated in this step include $H'_0$ and $Z'_0$. The parameters, obtained in the offline spectral calibration in Step 350 and used in this step include base copper ratios $R_h^0$ and $R_l^0$; three materials' base CT numbers $H_i^0$; three materials' base effective atomic numbers $Z_i^0$; three sets of material dependent coefficients, $m_h^H(i)$, $m_l^H(i)$, $m_h^Z(i)$, and $m_l^Z(i)$, $i=0,1,2$. Denote $H'_i$, $i=0,1,2$ as the three materials' working CT numbers (note that $H'_0$ is one of the generated offsets), and $Z'_i$, $i=0,1,2$ as the three materials' working effective atomic numbers (note that $Z'_0$ is one of the generated offsets). Similar to computing the air counts in the working air table, they are computed according to the working copper ratios $R_h$ and $R_l$ as follows, for $i=0,1,2$, $$H'_i = H_i^0 + \Delta_i^H$$

$$Z'_i = Z_i^0 + \Delta_i^Z$$

where $$\Delta_i^H = m_h^H(i)(R_h - R_h^0) + m_l^H(i)(R_l - R_l^0)$$

$$\Delta_i^Z = m_h^Z(i)(R_h - R_h^0) + m_l^Z(i)(R_l - R_l^0)$$

Denote $H_i^n$, $i=0,1,2$ as the nominal fixed CT numbers for the three materials, and $Z_i^n$, $i=0,1,2$ as the nominal fixed effective atomic numbers for the three materials. The scales then are calculated as follows, $$s_{H,H} = \frac{(H_1^n - H_0^n)(Z'_2 - Z'_0) - (H_2^n - H_0^n)(Z'_1 - Z'_0)}{(H'_1 - H'_0)(Z'_2 - Z'_0) - (H'_2 - H'_0)(Z'_1 - Z'_0)}$$

$$s_{H,Z} = \frac{(H'_1 - H'_0)(H_2^n - H_0^n) - (H'_2 - H'_0)(H_1^n - H_0^n)}{(H'_1 - H'_0)(Z'_2 - Z'_0) - (H'_2 - H'_0)(Z'_1 - Z'_0)}$$

$$s_{Z,H} = \frac{(Z_1^n - Z_0^n)(Z'_2 - Z'_0) - (Z_2^n - H_0^n)(Z'_1 - Z'_0)}{(H'_1 - H'_0)(Z'_2 - Z'_0) - (H'_2 - H'_0)(Z'_1 - Z'_0)}$$

$$s_{Z,Z} = \frac{(H'_1 - H'_0)(Z_2^n - Z_0^n) - (H'_2 - H'_0)(Z_1^n - Z_0^n)}{(H'_1 - H'_0)(Z'_2 - Z'_0) - (H'_2 - H'_0)(Z'_1 - Z'_0)}$$

Finally in Step 340, the spectral correction is performed on the reconstructed High-energy CT image $I_H (X, y)$ and Z image $I_Z (x, y)$, $x=0, \ldots X-1$, and $y=0, \ldots Y-1$ on a pixel-by-pixel basis. Note that the image size is X x Y pixels. Denote $I'_H (x, y)$ as the spectral corrected High-energy CT image, and $I'_Z (x, y)$ as the spectral corrected Z image. They are calculated as follows, $$I'_H(x,y) = H_0^n + s_{H,H}(I_H(x,y) - H'_0) + s_{H,Z}(I_Z(x,y) - Z'_0)$$

$$I'_Z(x,y) = Z_0^n + s_{Z,H}(I_H(x,y) - H'_0) + s_{Z,Z}(I_Z(x,y) - Z'_0)$$

Note that the scales and offsets do not change for images which belong to a same piece of baggage because the time taken to scan a single piece of baggage (a few seconds) is small when compared with the time course of the spectral drift (in the order of 10 minutes). The determination of the beginning and ending of a piece of baggage uses the method described in the assignee's co-pending patent "Method of and system for extracting 3D bag images from continuously reconstructed 2D image slices in computed tomography," invented by Zhengrong Ying, et al, U.S. application Ser. No. 10/864,619, filed on Jun. 9, 2004.

III. Spectral Calibration

In Step 350, an offline spectral calibration is preferably performed. The spectral calibration uses an IQP containing at least three materials: PVC (Poly-Vinyl Chloride), Teflon, and Nylon. The offline spectral calibration on each scanner requires three air scans (in the absence of any object inside the scanner) and three IQP (Image Quality Phantom) scans. Note that the three scans are performed at different settings of DC and AC voltages. The first scan is performed at DC and AC voltages corresponding to normal operation conditions, for example, DC=140 kV, and AC=40 kV. The rest of two scans correspond to different settings of the DC and AC voltages. For example, DC=135 kV, AC=40 kV for the second scan, and DC=140 kV, AC=36 kV for the third scan. Also note that each IQP scan immediately (within one minute) follows each air scan before the DC and AC change to the next setting.

The specific materials contained inside the IQP and the layout of these materials are described in detail in the assignee's co-pending patent "Method and apparatus for automatic image quality assessment," invented by Seemeen Karimi, et al, U.S. application Ser. No. 09/842,075, filed on Apr. 25, 2001.

The three air scans are performed to obtain the base air tables $A_l^0(v, s, r)$ and $A_h^0(v, s, r)$, air coefficients $m_{h,h}{}^A(v, s, r)$, $m_{h,l}{}^A(v,s,r)$, $m_{l,h}{}^A(v, s, r)$, and $m_{l,l,A}(v, r, s)$, and base copper ratios $R_h{}^0$ and $R_l{}^0$ used for generating working air tables.

Denote $P_{DAS}{}^j(v, s, r)$ as the detector readings of jth air scans, j=0,1,2, and $P_{off}(s, r)$ as the offset table. The offset corrected detector readings, denoted as $P_o{}^j(v, s, r)$, are calculated as follows, $$P_o^j(v,s,r) = P_{DAS}^j(v,s,r) - P_{off}(s,r)$$

The air tables for the three air scans, denoted as $A_l^j(v, s, r)$ and $A_h^j(v, s, r)$, j=0,1,2, are calculated as follows, $$A_l^j(v,s,r) = P_o^j(v,s,r), v \text{ is odd}$$

$$A_h^j(v,s,r) = P_o^j(v,s,r), v \text{ is even}$$

Note that $A_l^0(v, s, r)$ and $A_h^0(v, s, r)$ are the base air tables used in generating the working air tables in the online correction.

The copper ratios for the three air scans, denoted as $R_h^j$ and $R_l^j$, j=0,1,2, are calculated at according to Eqs. (a) and (b). Note that $R_h^0$ and $R_l^0$ are the base copper ratios used in the on-line correction.

Then the air coefficients $m_{h,h}{}^A(v, s, r)$, $m_{h,l}{}^A(v, s, r)$, $m_{l,h}{}^A(v, s, r)$, and $m^{l,l,A}(v, S, r)$ for each v, s, and r is calculated as follows, $$m_{h,h}^A(v, s, r) = \frac{(A_h^1(v, s, r) - A_h^0(v, s, r))(R_1^2 - R_1^0) - (A_h^2(v, s, r) - A_h^0(v, s, r))(R_1^1 - R_1^0)}{(R_h^1 - R_h^0)(R_1^2 - R_1^0) - (R_h^2 - R_h^0)(R_1^1 - R_1^0)}$$

$$m_{h,1}^A(v, s, r) = \frac{(R_h^1 - R_h^0)(A_h^2(v, s, r) - A_h^0(v, s, r)) - (R_h^2 - R_h^0)(A_h^1(v, s, r) - A_h^0(v, s, r))}{(R_h^1 - R_h^0)(R_1^2 - R_1^0) - (R_h^2 - R_h^0)(R_1^1 - R_1^0)}$$

$$m_{1,h}^A(v, s, r) = \frac{(A_1^1(v, s, r) - A_1^0(v, s, r))(R_1^2 - R_1^0) - (A_1^2(v, s, r) - A_1^0(v, s, r))(R_1^1 - R_1^0)}{(R_h^1 - R_h^0)(R_1^2 - R_1^0) - (R_h^2 - R_h^0)(R_1^1 - R_1^0)}$$

$$m_{1,1}^A(v, s, r) = \frac{(R_h^1 - R_h^0)(A_1^2(v, s, r) - A_1^0(v, s, r)) - (R_h^2 - R_h^0)(A_1^1(v, s, r) - A_1^0(v, s, r))}{(R_h^1 - R_h^0)(R_1^2 - R_1^0) - (R_h^2 - R_h^0)(R_1^1 - R_1^0)}$$

The three IQP scans then are performed to generate the three materials' base CT numbers $H_i^0$; three materials' base effective atomic numbers $Z_i^0$; three sets of material dependent coefficients, $m_h^Z(i)$, $m_l^Z(i)$, $m_h^H(i)$, and $m_h^H(i)$, i=0,1,2. The three materials used are preferably: Nylon cylinder, Teflon cylinder, and PVC cylinder inside the IQP. These three materials are indexed by i=0,1,2 in the order listed above. The three scans are indexed by j=0,1,2.

Each IQP scan produces a High-energy CT image and a Z image, these two images are analyzed using the method, described in the assignee's co-pending patent "Method and apparatus for automatic image quality assessment," invented by Seemeen Karimi, et al, U.S. application Ser. No. 09/842,075, filed on Apr. 25, 2001, incorporated herein by reference, to obtain the average CT number $H_i^j$ and average effective atomic number $Z_i^j$ for each material, i=0,1,2, and j=0,1,2. Note that among them $H_i^0$, i=0,1,2 are the base CT numbers and $Z_i^0$, i=0,1,2 are the three materials' base effective atomic numbers used in the online correction.

The three sets of the material dependent coefficients $m_h^H(i)$, $m_l^H(i)$, $m_h^Z(i)$, and $m_l^Z(i)$, i=0,1,2 are calculated as follows, $$m_h^H(i) = \frac{(H_i^1 - H_i^0)(R_1^2 - R_1^0) - (H_i^2 - H_i^0)(R_1^1 - R_1^0)}{(R_h^1 - R_h^0)(R_1^2 - R_1^0) - (R_h^2 - R_h^0)(R_1^1 - R_1^0)}$$

$$m_1^H(i) = \frac{(R_h^1 - R_h^0)(H_i^2 - H_i^0) - (R_h^2 - R_h^0)(H_i^1 - H_i^0)}{(R_h^1 - R_h^0)(R_1^2 - R_1^0) - (R_h^2 - R_h^0)(R_1^1 - R_1^0)}$$

$$m_h^Z(i) = \frac{(Z_i^1 - Z_i^0)(R_1^2 - R_1^0) - (Z_i^2 - Z_i^0)(R_1^1 - R_1^0)}{(R_h^1 - R_h^0)(R_1^2 - R_1^0) - (R_h^2 - R_h^0)(R_1^1 - R_1^0)}$$

$$m_1^Z(i) = \frac{(R_h^1 - R_h^0)(Z_i^2 - Z_i^0) - (R_h^2 - R_h^0)(Z_i^1 - Z_i^0)}{(R_h^1 - R_h^0)(R_1^2 - R_1^0) - (R_h^2 - R_h^0)(R_1^1 - R_1^0)}$$

While this disclosure has been particularly shown and described with references to preferred embodiments thereof, it will be understood by those skilled in the art that various changes in form and details may be made therein without departing from the spirit and scope of the disclosure as defined by the following claims. Such variations include using more than three materials and using more than three scans for the spectral calibration, obtaining base air tables using additional air calibration procedures, and using a training procedure to derive the necessary calibration parameters for all the scanners instead of using a scanner dependent spectral calibration procedure, as well as using the copper ratios to set the DC and AC voltages on the HVPS. Such variations also include using at least three individual materials scanned without using IQP during the offline spectral calibration, skipping the step of generating the working air tables, using other material instead of copper as the filter, and applying the online spectral corrections to other types of images, such as, photoelectric images, Compton images, and low-energy CT images.

The invention claimed is:

1. A method of correcting reconstructed images, reconstructed from projection data acquired while scanning objects with a scanner including a scanner detector array, for the spectral variation in multi-energy X-ray computed tomography using at least a portion of the same acquired projection data, wherein the projection data include at least a set of low-energy projections and a set high-energy projections obtained using at least two x-ray spectra, and wherein a filter is mounted relative to at least a portion but not the whole of the detector array, comprising:

A. Generating low-energy and high-energy working filter ratios respectively for each of the low-energy and high-energy projections, derived from data acquired by at least a portion of the detector array, and calculating spectral variation using low-energy and high-energy base filter ratios and the low-energy and high-energy working filter ratios;

B. Calculating working high-energy CT numbers and working effective atomic numbers as a function of the low-energy and high-energy working filter ratios, the low-energy and high-energy base filter ratios, and base high-energy CT numbers and base-effective atomic numbers for a set of three reference materials; and C. Calculating scales and offsets using the working high-energy CT numbers and the working effective atomic numbers and correcting the reconstructed images using the scales and offsets.

2. The method of claim 1, further including, a calibration procedure comprising: performing scans of each of the three reference materials at each of the three different pairs of low-energy and high-energy X-ray spectra, and measuring low-energy and high-energy base filter ratios, base high-energy CT numbers and base effective atomic numbers to generate parameters for step B.

3. The method of claim 2, wherein the three reference materials have different density and different atomic number.

4. The method of claim 1, wherein the reconstructed images include high-energy CT images, and step C includes correcting at least some of the high-energy CT images.

5. The method of claim 1, wherein reconstructed images derived from data acquired while scanning objects with a scanner include effective atomic number images, and step C includes correcting at least some of the effective atomic number images.

6. The method of claim 1, further including generating at least a low-energy working air table and a high-energy working air table, both corrected using the high and low energy working filter ratios.

7. A system for correcting reconstructed images, reconstructed from projection data acquired by a scanner including a detector array, while scanning objects for the spectral variation in multi-energy X-ray computed tomography using at least a portion of the same acquired projection data, wherein the projection data include at least a set of low-energy projections and a set of high-energy projections obtained using at least two x-ray spectra, and wherein a filter is mounted relative to at least a portion but not the whole of the detector array, comprising:

A. A subsystem configured and arranged so as to generate low-energy and high-energy working filter ratios for the respective low and high energy projections, all derived from data acquired by at least a portion of the detector array, and calculating spectral variation using low-energy and high-energy base filter ratios and the low-energy and high-energy working filter ratios;

B. A subsystem configured and arranged so as to calculate working high-energy CT numbers and working effective atomic numbers as a function of the low-energy and high-energy working filter ratios, the low-energy and high-energy base filter ratios and base high-energy CT numbers and base-effective atomic numbers for a set of three reference materials; and C. A subsystem configured and arranged so as to calculate scales and offsets from the working high-energy CT numbers and the working effective atomic numbers and correct the reconstructed images using the scales and offsets.

8. The system of claim 7, further including, a calibration subsystem constructed and arranged so as to perform scans of the three reference materials at three different pairs of low-energy and high-energy X-ray spectra, and measure low-energy and high-energy base filter ratios, base high-energy CT numbers and base effective atomic numbers to generate parameters for subsystem B.

9. The system of claim 7, wherein the reconstructed images include high-energy CT images and subsystem C is further configured and arranged so as to correct at least some of the high-energy CT images.

10. The system of claim 7, wherein the reconstructed images include effective atomic number images, and subsystem C is further configured and arranged so as to correct at least some of the effective atomic number images.

11. The system of claim 7, further including a subsystem configured and arranged so as to generate at least a low-energy working air table and a high-energy working air tables, both corrected using the generated high and low energy filter ratios.

* * * * *